(12) United States Patent
Jacobson et al.

(10) Patent No.: US 7,741,245 B2
(45) Date of Patent: Jun. 22, 2010

(54) METHOD FOR TREATING PLANTS OR PLANT PARTS

(75) Inventors: Richard Martin Jacobson, Chalfont, PA (US); Martha Jean Kelly, Collegeville, PA (US); Fiona Linette Wehmeyer, Roslyn, PA (US)

(73) Assignee: Rohm and Haas Company, Philadelphia, PA (US)

( * ) Notice: Subject to any disclaimer, the term of this patent is extended or adjusted under 35 U.S.C. 154(b) by 1127 days.

(21) Appl. No.: 11/157,107

(22) Filed: Jun. 20, 2005

(65) Prior Publication Data
US 2005/0288189 A1 Dec. 29, 2005

Related U.S. Application Data

(60) Provisional application No. 60/582,484, filed on Jun. 24, 2004.

(51) Int. Cl.
*A01N 25/00* (2006.01)
*A01N 63/00* (2006.01)
*A01N 35/00* (2006.01)

(52) U.S. Cl. .................. 504/116.1; 504/118; 504/189; 504/348

(58) Field of Classification Search ............. 504/116.1, 504/118, 348
See application file for complete search history.

(56) References Cited

U.S. PATENT DOCUMENTS

| | | | |
|---|---|---|---|
| 3,657,348 A | * | 4/1972 | Tobey .................. 568/303 |
| 3,860,720 A | * | 1/1975 | Covey .................. 514/455 |
| 5,496,568 A | * | 3/1996 | Winston .................. 424/717 |
| 5,518,988 A | | 5/1996 | Sisler et al. |
| 6,194,350 B1 | * | 2/2001 | Sisler .................. 504/114 |
| 2004/0077502 A1 | * | 4/2004 | Jacobson et al. ............. 504/313 |
| 2005/0065033 A1 | | 3/2005 | Jacobson |

OTHER PUBLICATIONS

M. Fediorynski, "Synthesis of Gem-Dihalocyclopropanes and Their Use in Organic Synthesis," Chem. Rev., vol. 103, pp. 1090-1132, 2003.
M. Nakamura, et al., "Cyclopropenone Acetals Synthesis and Reactions," Chem. Rev., vol. 103, pp. 1295-1326, 2003.
K. Komatsu, et al, "Cyclopropenylium Cations, Cyclopropenones, and Heteroanalogues—Recent Advances," Chem. Rev., vol. 103, pp. 1371-1427 2003.
A. Meijere, "Introduction: Cyclopropanes and Related Rings," Chem Rev, vol. 103, pp. 931-932, 2003.
W.E. Billups, et al, "Synthesis of Methylenecyclopropene," J. Amer. Chem.Soc., vol. 106, pp. 3698-3699, 1984.
S.W. Staley, et al, "Synthesis and Direct Observation of Methyenecyclopropene," J. Amer. Chem. Soc., vol. 106, pp. 3699-3700, 1984.
M. Isaka, et al, "Applications of Metalated Cyclopropenone Ketals in a General Synthesis of Cyclopropenones," J. Org. Chem., vol. 54, pp. 4727-4729, 1989.
M. Isaka, "General Synthesis of Cyclopropenones and Their Acetals," Tetrahedron, vol. 48, pp. 2045-2057, 1992.

* cited by examiner

*Primary Examiner*—Johann R Richter
*Assistant Examiner*—Kristie L Brooks
(74) *Attorney, Agent, or Firm*—Carl P. Hemenway

(57) ABSTRACT

The present invention generally relates to a method of treating plants or plant parts comprising the step of contacting said plants or plant parts with at least one composition comprising at least one double bond adducted cyclopropene compound.

10 Claims, No Drawings

METHOD FOR TREATING PLANTS OR PLANT PARTS

This application claims the benefit of U.S. Provisional Application No. 60/582,484, filed Jun. 24, 2004.

BACKGROUND

Plants and plant parts are subject to various biological processes such as, for example, ripening, maturation, and degradation. Altering biological processes in plants or plant parts by contacting them with one or more chemical compositions is known as plant growth regulation. It is often desirable to treat plants or plant parts by contacting them with one or more chemical compositions in order to desirably enhance or delay such processes. In some cases, for example, the process of interest is a response of the plant or plant part to ethylene, and it is sometimes desirable to inhibit such ethylene responses by contacting the plant or plant part with one or more compositions that inhibit the response to ethylene. For example, ethylene can cause the premature death of plants or plant parts including, for example, flowers, leaves, fruits, and vegetables; and ethylene can promote leaf yellowing, stunted growth, and premature fruit, flower, and leaf drop. Such responses are understood to involve interaction of ethylene with a specific ethylene receptor in the plant. Many compounds other than ethylene interact with this receptor: some mimic the action of ethylene; others prevent ethylene from binding and thereby counteract its action.

U.S. Pat. No. 5,518,988 to Sisler et al. ("Sisler") discloses the use of cyclopropene or 1.1.1. propellane or their derivatives for inhibiting an ethylene response in a plant. However, alternative compounds for treating plants are desired.

SUMMARY

In a first aspect of the present invention, there is provided a method of treating plants or plant parts comprising the step of contacting said plants or plant parts with at least one composition comprising at least one double bond adducted cyclopropene compound.

DETAILS

By "carbocyclic" is meant herein a chemical group that is a ring that contains only carbon atoms; by "heterocyclic" is meant herein that a ring that contains at least one heteroatom; by "heteroatom" is meant herein an atom other than carbon that is capable of bonding to at least two other atoms and is capable of being a member of a ring.

The practice of the present invention involves the use of certain compounds that are adducts of cyclopropene compounds. By "cyclopropene compound" is meant herein either cyclopropene or substituted cyclopropene. As used herein a "double bond adducted cyclopropene compound" is a cyclopropene compound in which one atom (called herein the "adduct atom of attachment") of a chemical group (called herein the "adduct chemical group") is attached to the number 3 carbon of the cyclopropene compound by a double bond. The number 1 and number 2 carbon atoms of the double bond adducted cyclopropene compounds (that is, the two carbon atoms within the cyclopropene ring that are connected to each other by a double bond) of the present invention may each independently be connected to a hydrogen or to a substituent chemical group.

It is contemplated that the adduct atom of attachment of a compound of the present invention will be further attached to the correct number of other atoms to satisfy the valence of the adduct atom of attachment. For example, in some embodiments, the adduct atom of attachment is oxygen, and it is not attached to any atom other than the number 3 carbon atom of the cyclopropene compound (that is, the oxygen atom is the entire adduct chemical group). For another example, in some embodiments, the adduct atom of attachment is nitrogen, and it is attached to one atom in the adduct chemical group and to the number 3 carbon atom of the cyclopropene compound. For an additional example, in some embodiments, the adduct atom of attachment is carbon, and it is attached to two atoms in the adduct chemical group and to the number 3 carbon atom of the cyclopropene compound.

In some embodiments, the double bond adducted cyclopropene compound of the present invention has 50 or fewer non-hydrogen atoms.

In some embodiments, the double bond adducted cyclopropene compound of the present invention is a neutral molecule. In other embodiments, the double bond adducted cyclopropene compound of the present invention is a salt.

Mixtures of suitable double bond adducted cyclopropene compounds are also suitable.

In some embodiments, at least one double bond adducted cyclopropene compound of the present invention present invention is a compound of the formula:

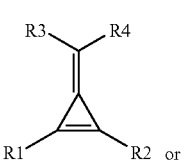

Structure 1

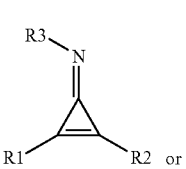

Structure 2

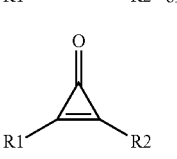

Structure 3 wherein: $R^1$, $R^2$, $R^3$ and $R^4$ are independently selected from H and a group of the formula:

wherein:
i) n is an integer from 1 to 12;
ii) each L is independently selected from a member of the group D1, D2, E, or J wherein:
  D1 is of the formula:

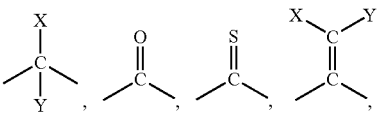

-continued

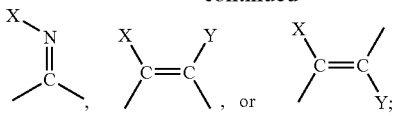

D2 is of the formula:

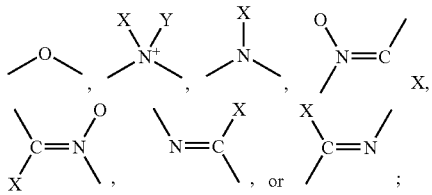

E is of the formula:

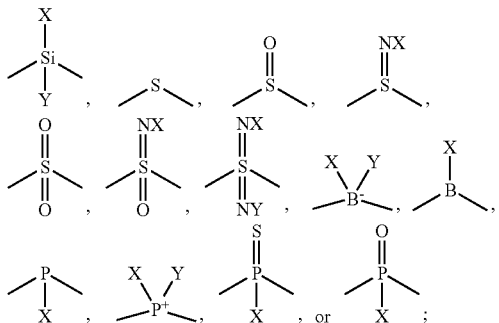

and
J is of the formula:

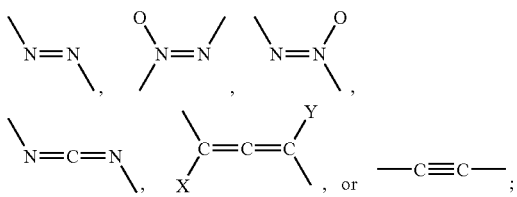

wherein:
A) each X and Y is independently a group of the formula:

-(L)$_m$-Z;

and
B) m is an integer from 0 to 8; and
C) no more than two D2 or E groups are adjacent to each other and no J groups are adjacent to each other;
iii) each Z is independently selected from:
A) hydrogen, halo, cyano, nitro, nitroso, azido, chlorate, bromate, iodate, isocyanato, isocyanido, isothiocyanato, pentafluorothio, or
B) a group G, wherein G is a 4 to 14 membered ring system.

For the purposes of this invention, in the structural representations of the various L groups, each open bond indicates a bond to another L group, a Z group, or the cyclopropene moiety. For example, the structural representation <chemical structure> indicates an oxygen atom with bonds to two other atoms; it does not represent a dimethyl ether moiety.

Also suitable as the double bond adducted cyclopropene compound of the present invention are, for example, stereoisomers of compounds that have structure 1, structure 2, or structure 3. Some compounds suitable as the double bond adducted cyclopropene compound of the present invention are, for example, enantiomers of compounds that have structure 1, structure 2, or structure 3.

Among embodiments in which at least one of $R^1$, $R^2$, $R^3$, and $R^4$ is present, is not hydrogen, and has n of 2 or larger, the L groups within that R, $R^2$, $R^3$, or $R^4$ group may be the same as the other L groups within that $R^1$, $R^2$, $R^3$, or $R^1$ group, or any number of L groups within that $R^1$, $R^2$, $R^3$, or $R^4$ group may be different from the other L groups within that $R^1$, $R^2$, $R^3$, or $R^4$ group.

Among embodiments in which at least one of $R^1$, $R^2$, $R^3$, and $R^4$ is present and contains more than one Z group, the Z groups within that $R^1$, $R^2$, $R^3$, or $R^4$ group may be the same as the other Z groups within that $R^1$, $R^2$, $R^3$, or $R^4$ group, or any number of Z groups within that $R^1$, $R^2$, $R^3$, or $R^4$ group may be different from the other Z groups within that $R^1$, $R^2$, $R^3$, or $R^4$ group.

The $R^1$, $R^2$, $R^3$, and $R^4$ groups, when present, are independently selected from the suitable groups. The $R^1$, $R^2$, $R^3$, and $R^4$ groups may be the same as each other, or any number of them may be different from the others.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be substituted or unsubstituted. Some suitable substituted aliphatic groups include, for example, acetylaminoalkenyl, acetylaminoalkyl, acetylaminoalkynyl, alkoxyalkoxyalkyl, alkoxyalkenyl, alkoxyalkyl, alkoxyalkynyl, alkoxycarbonylalkenyl, alkoxycarbonylalkyl, alkoxycarbonylalkynyl, alkylcarbonyloxyalkyl, alkyl(alkoxyimino)alkyl, carboxyalkenyl, carboxyalkyl, carboxyalkynyl, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylaminoalkyl, alkylsulfonylalkyl, alkylthioalkenyl, alkylthioalkyl, alkylthioalkynyl, haloalkylthioalkenyl, haloalkylthioalkyl, and haloalkylthioalkynyl.

Also among the suitable $R^1$, $R^2$, $R^3$, and $R^4$ groups are, for example, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, for example, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, for example, alkylphosphonato, dialkylphosphato, dialkylthiophosphato, dialkylamino, alkylcarbonyl, and dialkylaminosulfonyl.

Among the aliphatic groups suitable as $R^1$, $R^2$, $R^3$, or $R^4$ are, for example, cycloaliphatic groups, including, for example, cycloalkenyl, cycloalkyl, and cycloalkynyl. Suitable cycloaliphatic groups may be substituted or unsubstituted. Among the suitable substituted cycloaliphatic groups are, for example, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, haloalkylthiocycloalkenyl, haloalkylthiocycloalkyl, and haloalkylthiocycloalkynyl.

Also among the suitable $R^1$, $R^2$, $R^3$, and $R^4$ groups are, for example, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, for example, substituted and unsubstituted heterocyclyl groups (i.e., non-aromatic cyclic groups with at least one heteroatom in the ring). Among the suitable substituted heterocyclyl groups are, for example, alkenylheteroycycyl, alkylheteroycycyl, alkynylheteroycycyl, acetylaminoheterocyclyl, alkoxyalkoxyheterocyclyl, alkoxyheterocyclyl, alkoxycarbonylheterocyclyl, alkylcarbonyloxyheterocyclyl, carboxyheterocyclyl, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, and haloalkyllthioheterocyclyl.

Also among the suitable $R^1$, $R^2$, $R^3$, and $R^4$ groups are, for example, substituted and unsubstituted heterocyclyl groups that are connected to the double bond adducted cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted aryl groups. Some suitable substituted aryl groups are, for example, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, and haloalkylthioaryl.

Also among the suitable $R^1$, $R^2$, $R^3$, and $R^4$ groups are, for example, substituted and unsubstituted heteroaryl groups. Some suitable substituted heteroaryl groups are, for example, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarvlsulfonylalkyl, alkylthioheteroaryl, and haloalkylthioheteroaryl.

Also among the suitable $R^1$, $R^2$, $R^3$, and $R^4$ groups are, for example, substituted and unsubstituted heteroaryl groups that are connected to the double bond adducted cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 4 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring sysytems suitable as chemical group G may be monocyclic, bicyclic, tricyclic, polycyclic, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a 4 membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from chemical groups in the category X as defined herein below. Also suitable are embodiments in which G is a carbocyclic ring system.

Among the suitable G groups are, for example, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, pyridin-2-yl, pyridin-3 yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl and 5-methyl-6-chromanyl, adamantyl, norbornyl, and their substituted analogs such as, for example: 3-butyl-pyridin-2-yl, 4-bromo-pyridin-2-yl, 5-carboethoxy-pyridin-2-yl, and 6-methoxyethoxy-pyridin-2-yl.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

In some embodiments, the composition of the present invention includes at least one compound with structure 1. Among such embodiments are embodiments in which at least two of $R^1$, $R^2$, $R^3$, and $R^4$ are hydrogen. For example, in some embodiments, $R^1$ and $R^2$ are each hydrogen, and $R^3$ and $R^4$ are independently either hydrogen or $-(L)_n-Z$, as defined herein above. For another example, in some embodiments, $R^3$ and $R^4$ are each hydrogen, and $R^1$ and $R^2$ are independently either hydrogen or $-(L)_n-Z$, as defined herein above. Among such embodiments are embodiments in which at least three of $R^1$, $R^2$, $R^3$, and $R^4$ are hydrogen. For example, in some embodiments, $R^2$, $R^3$, and $R^4$ are each hydrogen, and $R^1$ is either hydrogen or $-(L)_n-Z$, as defined herein above. For another example, in some embodiments, $R^1$, $R^2$, and $R^3$ are each hydrogen, and $R^4$ is either hydrogen or $-(L)_n-Z$, as defined herein above.

In some embodiments, the composition of the present invention includes at least one compound with structure 2. Among such embodiments are embodiments in which $R^2$ is hydrogen.

In some embodiments, the composition of the present invention includes at least one compound with structure 3. Among such embodiments are embodiments in which $R^2$ is hydrogen.

In some embodiments (herein called "123 embodiments"), the composition of the present invention includes at least one compound with structure 1 or structure 2 or structure 3. Among 123 embodiments in which at least one of $R^1$, $R^2$, $R^3$, or $R^4$, is present and is not hydrogen are, for example, embodiments in which n is 1 to 8 and embodiments in which n is 1 to 7. Independently, among 123 embodiments that include one or more X or Y groups, included are embodiments in which m is 0 to 4 and embodiments in which m is 0 to 2. Independently, among 123 embodiments that include one or more D1 groups, included are embodiments in which D1 is —CXY—, —CO—, or —CS— and embodiments in which D1 is —CXY—. Independently, among 123 embodiments that include one or more D2 groups, included are embodiments in which D2 is —O— or —NX—. Independently, among 123 embodiments that include one or more E groups, included are embodiments in which E is —S—, —SiXY—, or —SO$_2$—. Independently, among 123 embodiments that include one or more X or Y groups, included are embodiments in which each X and Y, if present, is selected independently from hydrogen, halo, —OH, —SH, —C(O)($C_1$-$C_4$)alkyl-, —C(O)O($C_1$-$C_4$)alkyl, —O—($C_1$-$C_4$)alkyl, —S—($C_1$-$C_4$)alkyl, and substituted or unsubstituted —($C_1$-$C_4$)alkyl. Independently, among 123 embodiments that include one or more Z groups, included are embodiments in which each Z is selected independently from hydrogen, halo, and G; also included are embodiments in which each Z is selected independently from hydrogen and G.

In some embodiments, treatment of plants or plant parts with the method of the present invention results in plant growth regulation. In some embodiments, treatment of plants or plant parts with the method of the present invention results in one or more of the following effects: inhibiting abscission in a plant, prolonging the life of a cut flower, and inhibiting the ripening of a picked fruit or vegetable. While the invention is not limited to a particular mechanism, it is contemplated that in some embodiments, the method of the present invention affects one or more biological processes in the plant or plant part by blocking ethylene receptors in the plants or plant parts.

The methods described herein may be carried out in a variety of ways, such as by contacting the plant with a cyclopropene derivative or a composition thereof, whether in solid, liquid, or gaseous form, or by exposing the plant or plant part. For the purposes of this invention, "contacting" means to bring the double bond adducted cyclopropene compound and a plant or plant part into intimate association with each other such that a sufficient number of ethylene receptors are effected by the cyclopropene.

In some embodiments, the composition of the present invention contains no other compounds in addition to the double bond adducted cyclopropene compound or compounds.

In other embodiments, the composition of the present invention contains at least one compound that is not a double bond adducted cyclopropene compound. In some of the embodiments in which the composition of the present invention contains at least one compound in addition to the double bond adducted cyclopropene compound or compounds, the amount of double bond adducted cyclopropene compound in the composition is 0.005% or more; or 1% or more; or 2% or more; or 3% or more; or 4% or more; by weight based on the total weight of the composition. Independently, in some of the embodiments in which the composition of the present invention contains at least one compound in addition to the double bond adducted cyclopropene compound or compounds, the amount of double bond adducted cyclopropene compound in the composition is 99% or less; or 95% or less; or 90% or less; or 80% or less; or 70% or less; by weight based on the total weight of the composition.

In some of the embodiments in which the composition of the present invention contains at least one compound in addition to the double bond adducted cyclopropene compound or compounds, these compositions may contain, for example, one or more adjuvants, such as, for example, carriers, extenders, binders, lubricants, surfactants and/or dispersants, wetting agents, spreading agents, dispersing agents, stickers, adhesives, defoamers, thickeners, and emulsifying agents. Some of such adjuvants commonly used in the art can be found in the John W. McCutcheon, Inc. publication *Detergents and Emulsifiers, Annual*, Allured Publishing Company, Ridgewood, N.J., U.S.A.

In some embodiments of the present invention, the only compounds present in the composition that are effective as plant growth regulators are double bond adducted cyclopropene compounds. In other embodiments, one or more effective plant growth regulators that are not double bond adducted cyclopropene compounds (such as, for example, single bond adducted cyclopropene compounds, as disclosed by Sisler) are included in the composition of the present invention in addition to the double bond adducted cyclopropene compound or compounds.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

In some embodiments, the composition of the present invention includes at least one liquid, which may, for example, act as a carrier for the other ingredients of the composition, either as a solvent or as a dispersion medium for carrying dispersed ingredients or as both a solvent and a dispersion medium. Water is a suitable carrier. Other suitable carriers are, for example, organic solvents, such as, for example, hydrocarbons such as hexane, benzene, toluene, xylene, kerosene, diesel oil, fuel oil and petroleum naphtha; ketones such as acetone, methyl ethyl ketone and cyclohexanone; chlorinated hydrocarbons such as methylene chloride; esters such as ethyl acetate, amyl acetate, and butyl acetate; ethers such as ethylene glycol monomethyl ether and diethylene glycol monomethyl ether; alcohols, such as, ethanol, methanol, isopropanol, amyl alcohol, ethylene glycol, propylene glycol, butyl carbitol acetate, and glycerine. Mixtures of water and organic solvents can also be employed as carriers for the active compounds.

Solid, liquid, and gaseous compositions can be prepared by various conventional procedures. Thus, the active ingredient (i.e., the double bond adducted cyclopropene compound), in finely divided form if a solid, may be tumbled together with finely divided solid carrier. Alternatively, the active ingredient in liquid form, including mixtures, solutions, dispersions, emulsions and suspensions thereof, may be admixed with a solid carrier in finely divided form. Furthermore, the active ingredient in solid form may be admixed with a liquid carrier to form a mixture, solution, dispersion, emulsion, suspension or the like.

The composition of the present invention can be applied to plants by any means. The compositions may be applied in gaseous, liquid, or solid form by contacting the composition with the plant to be treated. Some compositions include an inert carrier. When in gaseous form, the double bond adducted cyclopropene compound may be dispersed in air or in an inert gaseous carrier to provide a gaseous solution. The double bond adducted cyclopropene compound may also be suspended in a liquid solution such as an organic solvent or an aqueous solution that may serve as the inert carrier. Compositions containing the active compound may be heterogeneous or homogeneous and may be of various forms including solutions, mixtures, dispersions, emulsions, suspensions, combinations thereof, and the like.

The double bond adducted cyclopropene compound may also be encapsulated into a molecular encapsulation agent. Encapsulating agents include, for example, cyclodextrins, crown ethers, polysiloxanes, and zeolites. In some embodiments, encapsulating agents include, for example, one or more of α-cyclodextrin, β-cyclodextrin, and γ-cyclodextrin. The most preferred encapsulating agent will vary depending upon the size of the substituents on the double bond adducted cyclopropene compound. As one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors. When encapsulated, the preferred concentrations of the cyclopropenes will typically be less than in other compositions due to the capacity limitations of molecular encapsulation agents.

The compositions of the present invention can also be applied as aerosols, e.g., by dispersing them in air using a compressed gas such as, for example, nitrogen, carbon dioxide, dichlorodifluoromethane, trichlorofluoromethane, or other halocarbons.

In some of the embodiments in which the double bond adducted cyclopropene compound is in gaseous form when it contacts plants or plant parts, useful concentration of double bond adducted cyclopropene compound (measured volume/volume, "v/v") in the atmosphere in contact with the plants or plant parts is from about 0.1 part per billion ("ppb") to 10,000 parts per million ("ppm").

In some embodiments, the double bond adducted cyclopropene compound is in a liquid form when it contacts plants or plant parts. Liquid form, as used herein, includes solutions and dispersed forms, as discussed herein above. In some embodiments, the double bond adducted cyclopropene compound in the liquid form will be encapsulated in an encapsulating agent. In other embodiments, the double bond adducted cyclopropene compound will not be encapsulated in an encapsulating agent; or some of the double bond adducted cyclopropene compound may be encapsulated while some of the double bond adducted cyclopropene compound is not encapsulated. In some of the embodiments in which the double bond adducted cyclopropene compound is in a liquid form when it contacts plants or plant parts, the concentration of double bond adducted cyclopropene compound (by weight, based on the weight of the composition) is from about 0.01 part per billion ("ppb") to 10,000 parts per million ("ppm").

In some embodiments in which the composition of the present invention is applied as a liquid, at least one double bond adducted cyclopropene compound is dissolved in solvent to form a solution. Water and water/acetone mixtures (for example, 10% acetone and 90% water by weight based on the weight of solvent) are suitable solvents. In some embodiments, one or more adjuvants, such as, for example, surfactant, is also added to the solution. In some embodiments, such a solution is contacted with plants or plant parts by spraying. One method of spraying is using an atomizer such as, for example, a DeVilbiss atomizer.

The term "plant or plant part" is used in a generic sense herein, and includes, for example, woody-stemmed plants such as trees and shrubs; herbs; vegetables, fruits, and agricultural crops; ornamental plants; and parts thereof. Plants to be treated by the methods described herein include whole plants and any parts thereof, such as field crops, potted plants, seeds, cut flowers (stems and flowers), and harvested fruits and vegetables.

Plants treated with the compounds and by the methods of the present invention are preferably treated with a non-phytotoxic amount of double bond adducted cyclopropene compound.

Among the uses of the present invention are, for example, plant growth regulation. Also among the uses of the present invention are, for example, modifying a variety of ethylene responses such as, for example, the ripening and/or senescence of flowers, fruits, and vegetables; abscission of foliage, flowers, and fruit; the shortening of life of ornamentals such as potted plants, cut flowers, shrubbery, seeds, and dormant seedlings; in some plants (e.g., pea) the inhibition of growth, the stimulation of growth (e.g., rice), auxin activity, inhibition of terminal growth, control of apical dominance, increase in branching, increase in tillering, changing the morphology of plants, modifying the susceptibility to plant pathogens such as fungi, changing bio-chemical compositions of plants (such as increasing leaf area relative to stem area), abortion or inhibition of flowering and seed development, lodging effects, stimulation of seed germination and breaking of dormancy, and hormone or epinasty effects.

The compounds of this invention can be prepared by any method. Some known methods can be found, for example, in the following publications: "General synthesis of cyclopropenones and their acetals," by Masahiko Isaka, Satoshi Ejiri, and Eiichi Nakamura, in Tetrahedron 1992, vol. 48, no. 11, pages 2045-2057; "Cyclopropenone Acetals Synthesis and Reactions," by Masaharu Nakamura, Hiroyuki Isobe, and Eiichi Nakamura, in Chem. Rev. 2003, vol. 103, pages 1295-1326; "Synthesis of Methylenecyclopropene," by W. E. Billups, Long-Jin Lin, and Edward W. Casserly, in J. Am. Chem. Soc. 1984, vol. 106, pages 3698-3699; "Synthesis and Direct Observation of Methylenecyclopropene," by Stuart W. Staley and Timothy D. Norden, in J. Am. Chem. Soc. 1984, vol. 106, pages 3699-3700; and "Applications of Metalated Cyclopropenone Ketals in a General Synthesis of Cyclopropenones. An Efficient Synthesis of the Antibiotic Penitricin," by Masahiko Isaka, Satoshi Matsuzawa, Shigeru Yamago, Satoshi Ejiri, Yoshimitsu Miyachi, and Eiichi Nakamura," in J. Org. Chem. 1989, vol. 54, pages 4727-4729.

Example A

Synthesis of 2,2-bis-chloromethyl-5,5-dimethyl-1,3-dioxolane

This compound was synthesized by substantially following the procedure of the above-mentioned article by Isaka, Ejiri, and Nakamura. 69 grams of neopentyl glycol, 76 grams of 1,3-dichloroacetone, 50 ml of benzene, and 2.3 g of p-toluenesulfonic acid were refluxed through a Dean-Stark water separator for 8 hours whereon the reaction was diluted with hexanes and neutralized with aqueous sodium bicarbonate. The organic layer was dried over anhydrous magnesium sulfate and concentrated in vacuo yielding 41.2 g of 2,2-bis-chloromethyl-5,5-dimethyl-1,3-dioxolane, a pale yellow liquid.

Example B

Synthesis of 1-octylcycloprop-1-en-2-one neopentyl glycol ketal

This compound was synthesized by substantially following the procedure of the above-mentioned article by Isaka, Ejiri, and Nakamura. 4.23 grams of sodium amide was placed in a 300 ml flask under an atmosphere of dry nitrogen. 45 ml of anhydrous ammonia was condensed into the flask held at −78° C., and then 6.82 grams of the compound from Example A and 20 ml of diethyl ether was added via syringe. Then the reaction was allowed to warm and refluxed for 1 hour. The reaction mixture was recooled to −78° C., and 8.07 grams of 1-iodooctane in 10 ml of diethyl ether was added over 45 minutes. After a further. 10 minutes at −78° C., the reaction was again warmed and allowed to reflux for 30 minutes. The reaction was quenched with ammonium chloride, 50 ml of diethyl ether was added, and the remaining ammonia was allowed to boil away. Aqueous workup and chromatography yielded 3.6 grams of 1-octylcycloprop-1-en-2-one neopentyl glycol ketal.

Example 1

Synthesis of 1-octylcycloprop-1-en-2-one. ("OCPO")

This compound was synthesized by substantially following the procedure of the above-mentioned article by Isaka, Ejiri, and Nakamura. 1.01 gram of the compound from Example B was dissolved in 6 ml of tetrahydrofuran and one drop of water. 100 mg of Amberlyst™ 15 polymeric catalyst (from Rohm and Haas Company) was added and stirred for 6 hours. Filtration, concentration in vacuo, and column chromatography on silica gel eluting with 1:1 ethyl acetate/hexanes gave 500 mg of OCPO.

OCPO has the formula

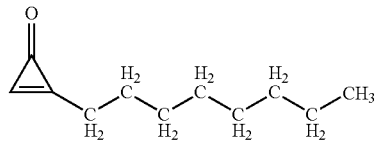

The biological activity of OCPO was assessed with the Tomato Epinasty Test. Epinasty is downward bending of leaves. The test was performed as follows.

Test plants are Patio variety tomato seedlings planted two plants per three inch square plastic pot. Volatile gas treatment entailed placing two pots of Patio variety tomatoes into a polystyrene 4.8 L volume treatment chamber along with one-half (upper or lower section) of a 50×9 mm plastic Petri dish containing a Gelman filter pad. OCPO, dissolved in 1.0 ml acetone, was pipetted onto the filter pad and the chamber was immediately sealed. The amount of OCPO was calculated to give concentration of 1000 ppm v/v of OCPO in the air of the sealed chamber. Four hours later ethylene gas was injected into the sealed chamber in an amount to give concentration of ethylene of 10 ppm v/v final concentration in the sealed chamber. Sixteen hours later the chambers were opened in an exhaust hood, allowed to air, and the plants scored visually for the degree of protection against ethylene-induced epinasty conferred by the experimental compound when compared to untreated controls on a scale of 0 to 10. A rating of 10 means complete protection. A rating of 0 means no protection from the effects of ethylene.

OCPO gave protection of ethylene-induced epinasty with rating of 7. The tomato plants exposed to ethylene but with no treatment with compounds of the present invention were rated 0.

We claim:

1. A method of inhibiting an ethylene response in plants or plant parts comprising the step of contacting said plants or plant parts with at least one composition comprising at least one double bond adducted cyclopropene compound, wherein said double bond adducted cyclopropene compound has the formula of

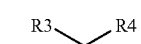

Structure 1

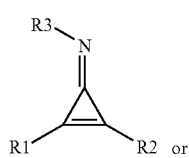

Structure 2

-continued

Structure 3

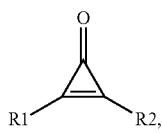

wherein:
a) each $R^1$, $R^2$, $R^3$ and $R^4$ is independently selected from the group consisting of H and a chemical group of the formula:

-(L)$_n$-Z wherein:
i) n is an integer from 1 to 12;
ii) each L is independently selected from the group consisting of D1, D2, E, and J, wherein:
D1 is of the formula:

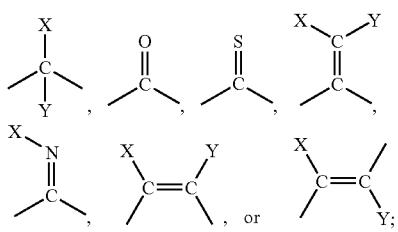

D2 is of the formula:

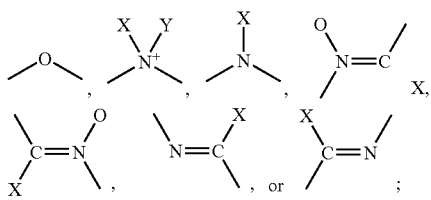

E is of the formula:

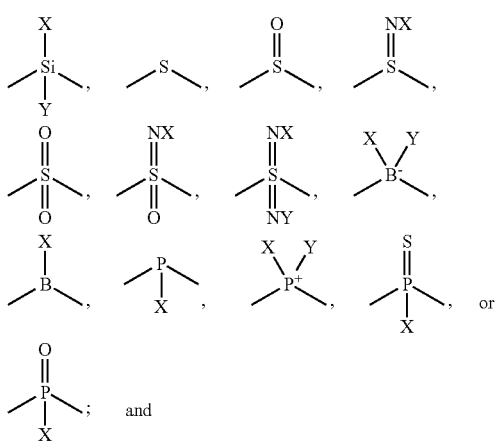

J is of the formula:

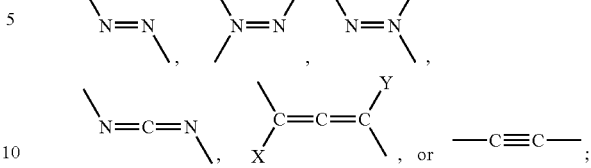

wherein:
A) each X and Y is independently a chemical group of the formula:

-(L)$_m$-Z;

and
B) m is an integer from 0 to 8; and
C) no more than two D2 or E groups are adjacent to each other and no J groups are adjacent to each other;
iii) each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 4 to 14 membered ring system; and
iv) the total number of heteroatoms in -(L)$_n$-Z is from 0 to 6; and
b) the total number of non-hydrogen atoms in said compound is 50 or less, with the proviso that each said double bond adducted cyclopropene compound that has said structure 3 has $R^2$ that is hydrogen.

2. The method of claim 1, wherein said compound inhibits an ethylene response in at least one of said plants or plant parts.

3. The method of claim 2, wherein said ethylene response is one or more response selected from the group consisting of: ripening or senescence of flowers, fruits, or vegetables; abscission of foliage, flowers, or fruit; shortening of life of ornamental plants, cut flowers, shrubbery, seeds, or dormant seedlings; inhibition of growth; stimulation of growth; auxin activity; inhibition of terminal growth; control of apical dominance; increase in branching; increase in tillering; changing the morphology of plants; modifying the susceptibility to plant pathogens; changing bio-chemical compositions; abortion or inhibition of flowering or seed development; lodging effects; stimulation of seed germination; breaking of dormancy; hormone effects; and epinasty effects.

4. The method of claim 1, wherein said double bond adducted cyclopropene compound comprises one or more compound having said structure 1.

5. The method of claim 1, wherein said double bond adducted cyclopropene compound comprises one or more compound having said structure 2.

6. The method of claim 1, wherein said double bond adducted cyclopropene compound comprises one or more compound having said structure 3.

7. The method of claim 1, wherein every said $R^2$ is a hydrogen.

8. The method of claim 1, wherein said plants or plant parts comprise harvested fruits and vegetables.

9. The method of claim 1, wherein said double bond adducted cyclopropene compound is encapsulated in a molecular encapsulating agent.

10. The method of claim 1, wherein said treating is performed by contacting said double bond adducted cyclopropene compound in gaseous form to said plants or plant parts.

* * * * *